(12) United States Patent
Hubbell et al.

(10) Patent No.: US 6,858,229 B1
(45) Date of Patent: Feb. 22, 2005

(54) IN SITU FORMING HYDROGELS

(75) Inventors: Jeffrey A. Hubbell, Zumikon (CH); Julia A. Kornfield, Pasadena, CA (US); Giyoong Tae, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/559,984

(22) Filed: Apr. 26, 2000

Related U.S. Application Data

(60) Provisional application No. 60/131,164, filed on Apr. 26, 1999.

(51) Int. Cl.[7] .......................... A61F 2/00; A61F 13/00; A61K 9/14
(52) U.S. Cl. ...................... 424/484; 424/422; 424/423; 424/486; 424/487; 424/488
(58) Field of Search .............................. 424/484, 486, 424/487, 488, 422, 423; 525/54.2

(56) References Cited

U.S. PATENT DOCUMENTS

| | | | |
|---|---|---|---|
| 5,278,201 A | | 1/1994 | Dunn et al. .................. 523/113 |
| 5,324,775 A | * | 6/1994 | Rhee et al. ................. 525/54.2 |
| 5,560,929 A | | 10/1996 | Hedstrand et al. ........... 424/486 |
| 5,976,648 A | | 11/1999 | Li et al. ..................... 428/34.9 |
| 6,218,464 B1 | * | 4/2001 | Parker et al. ............... 524/805 |
| 6,281,400 B1 | * | 8/2001 | Harmer et al. ............... 585/457 |

OTHER PUBLICATIONS

Amiel et al., "New associating polymer systems involving water soluble β–cyclodextrin polymers," *J. Inclusion Phen. & Mol. Recog.* 25:61–67, 1996.

Hill–West et al., "Inhibition of thrombosis and intimal thickening by in situ photopolymerization of thin hydrogel barriers," *Proc. Natl. Acad. Sci. USA* 91:5967–5971, 1994.

Hubbell, *MRS Bulletin*, "In Situ Material Transformations in Tissue Engineering," Nov. issue 33–35, 1996.

Jeong et al., "Biodegradable block copolymers as injectable drug–delivery systems," *Nature* 388:860–862, 1997.

Jordal et al., "Hydrolysis of Cyclodexctin by Aspergillus oryzae α–Amylase," *Starch/Starke* 36:140–143, 1984.

Rosenblatt et al., "A new injectable, in–situ cross–linkable collagen biomaterials," *Fifth World Biomaterials Congress* 344, 1996.

Saha et al., "Cyclodextrin Degrading Enzymes," *Starch/Starke* 44:312–315, 1992.

Sawhney et al., "Optimization of photopolymerized bio-erodible hydrogel properties for adhesion prevention,"*J. Biomed. Mater. Res.* 28:831–838, 1994.

Shieh et al., "Properties and Applications of Cyclodextrins," *Pure Appl. Chem.* A33:673–683, 1996.

Zhang et al., "Biodegradable of Aromatic Hydrocarbons in Soil–water Slurries: Experimental and Model Studies," *Abstract of the American Chemical Society Meeting* 36(1):245–247, 1996.

* cited by examiner

*Primary Examiner*—Thurman K. Page
*Assistant Examiner*—S. Tran
(74) *Attorney, Agent, or Firm*—Clark & Elbing LLP; Kristina Bieker-Brady, P.C.

(57) ABSTRACT

The invention features materials and methods for the liquid to solid transition of an injectable pre-hydrogel composition to a hydrogel. These methods can be carried out in situ.

18 Claims, 4 Drawing Sheets

IN SITU FORMING HYDROGELS

CROSS REFERENCE TO RELATED APPLICATIONS

This application claims priority from U.S. Provisional Application Ser. No. 60/131,164, filed Apr. 26, 1999.

BACKGROUND OF THE INVENTION

The present invention relates to materials and methods for inducing in situ transitions of a hydrogel precursor compositions from an injectable state to a hydrogel.

A mechanism for gently transitioning a hydrogel precursor composition from a liquid state to a solid state such that the transition can be carried out in situ, directly in intimate contact with sensitive biological materials, is of special interest for medical purposes. After being delivered in a liquid state, the in situ formation of a hydrogel at an implantation site has two potential advantages: the ability to match the morphology of a material implant to various complex tissue shapes in the body, and the ability to deliver a large device through a small hole in the body via minimally invasive surgery (Hubbell, MRS Bulletin, November issue, 33-35, 1996). In addition, this type of transitioning system can be used as a carrier for the controlled release of drugs, for the delivery of living cells in cell transplantation, as a barrier for the prevention of postoperative adhesions, or as a structural support at tissue sites.

SUMMARY OF THE INVENTION

We have developed methods and materials for the transition of a hydrogel precursor composition to a hydrogel. These methods and materials are sufficiently gentle that the transition can be carried out in situ, for example in direct contact with a tissue. The methods of the invention can be performed without the use of any complex instrumentation or high temperatures that might otherwise be harmful to the tissue at the site where the gel forms. The hydrogels that result from these methods possess high mechanical strength, and degradation rates that are of therapeutic use. In addition, these hydrogel precursors can be constructed to form in a manner that is selective for the intended target site, i.e., the transition to the precursor composition a hydrogel state can be controlled so that undesired chemical reactions with surrounding tissues do not occur.

In a first aspect, the invention features a hydrogel precursor composition comprising a polymer, wherein the polymer comprises a water soluble polymer domain with at least two hydrophobic interacting groups attached to it, and wherein the polymer is capable of assembling into a hydrogel under physiological conditions. The hydrogel precursor composition also comprises a physical chemical protecting group that prevents gelation of the hydrogel precursor composition until desirable.

In a second aspect, the invention features a hydrogel or hydrogel precursor composition comprising a polymer, wherein the polymer comprises a water soluble polymer domain with at least two hydrophobic interacting groups attached to it, and wherein the polymer is capable of assembling into a hydrogel under physiological conditions. The hydrogel or hydrogel precursor composition also comprises a physical chemical protecting group that prevents gelation of the hydrogel precursor composition or hydrogel. The hydrogel or hydrogel precursor composition further comprises a molecule that disrupts an interaction between the physical chemical protecting group and the hydrophobic interacting groups.

In one embodiment of the above two aspects of the invention, the polymer domain comprises poly(ethylene glycol) (PEG), poly(vinyl alcohol), poly(vinyl pyrrolidone), poly(ethyl oxazoline), poly(acrylic acid), poly(acrylamide), poly(styrene sulfonate), poly(amino acids), polysaccharides, or copolymers thereof. Preferably the polymer domain comprises poly(ethylene glycol). In another embodiment, the hydrophobic interacting groups are hydrocarbons, preferably perfluorinated hydrocarbons. In yet another embodiment, the physical chemical protecting group is cyclodextrin, preferably β-cyclodextrin.

In other embodiments, the physical chemical protecting group is a molecule that covalently binds to the hydrophobic interacting group. Preferably the molecule is hydrophilic. The polymer of the first or second aspects may be linear or branched, and may comprise a multi-arm poly(ethylene glycol). The hydrophobic interacting groups may be positioned at the termini of the polymer domain, or within the polymer domain. The linkage between the polymer domain and the hydrophobic interacting groups may be stable or degradable. Preferably the degradable linkage is an anhydride linkage, an ester linkage, a carbonate linkage, an amide linkage, or an oligomeric linkage. In a preferred embodiment, the oligomeric linkage comprises oligomers of lactic acid, glycolic acid, or epsilon-caproic acid, or oligomers of trimethylene carbonate, or co-oligomers thereof.

In other embodiments, the hydrophobic interacting groups interact with the physical chemical protecting group through a noncovalent bond. Preferably the interaction occurs by the formation of an inclusion complex.

In still other embodiments, the molecule that disrupts an interaction between the physical chemical protecting group and the hydrophobic interacting groups is a molecule that binds to the physical chemical protecting group better than the hydrophobic interacting groups bind to the physical chemical protecting group. Preferably the molecule that disrupts an interaction between the physical chemical protecting group and the hydrophobic interacting groups is a one-end modified polymer domain. Most preferably the one-end modified polymer domain comprises poly(ethylene glycol), and is modified with a perfluorinated hydrocarbon.

In still other embodiments, the molecule that disrupts an interaction between the physical chemical protecting group and the hydrophobic interacting groups is a molecule that degrades the linkage between the physical chemical protecting group and the hydrophobic interacting groups, or is a molecule that degrades the physical chemical protecting groups themselves. Most preferably a molecule that degrades the physical chemical protecting group is α-amylase or amyloglucosidase.

In one embodiment of the second aspect of the invention, the polymer domain comprises poly(ethylene glycol), the hydrophobic interacting groups are perfluorinated hydrocarbons, and the chemical protecting group is β-cyclodextrin.

In a third aspect, the invention features a method for forming a hydrogel in contact with a tissue, involving providing a solution comprising a polymer, wherein the polymer comprises a water soluble polymer domain with at least two hydrophobic interacting groups attached to it, and wherein the polymer is capable of assembling into a hydrogel under physiological conditions, and a physical chemical protecting group that prevents gelation of the polymer. In addition, the method involves providing a molecule that disrupts an interaction between the physical chemical protecting group and the hydrophobic interacting groups. The solution is combined with the molecule that disrupts an interaction between the physical chemical protecting group and the hydrophobic interacting groups, and prior to, during, or after this combining, the solution and the molecule that disrupts an interaction between the physical chemical protecting group and the hydrophobic interacting groups are contacted with a tissue. Finally, the solution is allowed to gel in contact with the tissue.

In a fourth aspect, the invention features a method for forming a hydrogel in contact with a tissue. The method involves providing a solution comprising a polymer, wherein the polymer comprises a water soluble polymer domain with at least two hydrophobic interacting groups attached to it, and wherein the polymer is capable of assembling into a hydrogel under physiological conditions, and a water soluble organic solvent that prevents gelation of the polymer. The method further involves removing all or part of the organic solvent from the solution, and prior to, during, or after this removal, the solution and organic solvent are contacted with a tissue. Finally, the mixture is allowed to gel in contact with the tissue.

In a fifth aspect, the invention features a method for forming a hydrogel in contact with a tissue. This method involves providing a solution comprising a polymer, wherein the polymer comprises a water soluble polymer domain with at least two hydrophobic interacting groups attached to it, and wherein the polymer is capable of assembling into a hydrogel under physiological conditions, and a water soluble organic solvent that prevents gelation of the polymer. The method also involves contacting the solution with a tissue, and allowing gelation of the mixture in contact with the tissue.

In a sixth aspect, the invention features a method for incorporating a sensitive biological material into a hydrogel composition, involving providing a solution comprising a polymer, wherein the polymer comprises a water soluble polymer domain with at least two hydrophobic interacting groups attached to it, and wherein the polymer is capable of assembling into a hydrogel under physiological conditions, and a physical chemical protecting group that prevents gelation of the polymer. The method further involves providing a molecule that disrupts an interaction between the physical chemical protecting group and the hydrophobic interacting groups, and providing a sensitive biological material. The sensitive biological material is combined with either the solution or with the molecule that disrupts an interaction between the physical chemical protecting group and the hydrophobic interacting groups. The solution with the molecule that disrupts an interaction between the physical chemical protecting group and the hydrophobic interacting groups and the sensitive biological material are then combined to form a mixture, and allowed to gel.

In a seventh aspect, the invention features a method for incorporating a sensitive biological material into a hydrogel composition. The method involves, providing a solution comprising a polymer, wherein the polymer comprises a water soluble polymer domain with at least two hydrophobic interacting groups attached to it, and wherein the polymer is capable of assembling into a hydrogel under physiological conditions, and an organic solvent that prevents gelation of the polymer. The method also involves providing a sensitive biological material. The sensitive biological material is combined with the solution to form a mixture, and prior to, during, or after, the combining, all or part of the organic solvent is removed from the solution. Finally, the solution is allowed to gel.

In an eighth aspect, the invention features a method for incorporating a sensitive biological material into a hydrogel composition, involving providing a solution comprising a polymer, wherein the polymer comprises a water soluble polymer domain with at least two hydrophobic interacting groups attached to it, and wherein the polymer is capable of assembling into a hydrogel under physiological conditions, and an organic solvent that prevents gelation of the polymer, and providing a sensitive biological material. The sensitive biological material is combined with the solution to form a mixture, and prior to, during, or after the combining, the solution and/or said sensitive biological material is contacted with a tissue. Gelation is then allowed to occur.

In one embodiment of the sixth or seventh or aspect of the invention, prior to gelation, the mixture is contacted with a tissue. Preferably prior to, during, or after formation of the mixture, one or more components of the mixture is contacted with a tissue.

In one embodiment of any of the third through eighth aspects of the invention, the polymer domain comprises poly(ethylene glycol) (PEG), poly(vinyl alcohol), poly(vinyl pyrrolidone), poly(ethyl oxazoline), poly(acrylic acid), poly (acrylamide), poly(styrene sulfonate), poly(amino acids), polysaccharides, or copolymers thereof. Preferably the polymer domain comprises poly(ethylene glycol). In another embodiment, the hydrophobic interacting groups are hydrocarbons, preferably perfluorinated hydrocarbons. Preferably the polymer domain comprises poly(ethylene glycol), the hydrophobic interacting groups are perfluorinated hydrocarbons.

In other embodiments of any of the third through eighth aspects of the invention, the polymer is linear or branched. The branched polymer may comprise a multi-arm poly (ethylene glycol). The hydrophobic interacting groups may be positioned at the termini of the polymer domain, or within the polymer domain. The linkage between the polymer domain and the hydrophobic interacting groups may be stable or degradable. Preferably the degradable linkage is an anhydride linkage, an ester linkage, a carbonate linkage, an amide linkage, or an oligomeric linkage. In a preferred embodiment, the oligomeric linkage comprises oligomers of lactic acid, glycolic acid, or epsilon-caproic acid, or oligomers of trimethylene carbonate, or co-oligomers thereof.

In preferred embodiments of the third or sixth aspect of the invention, the physical chemical protecting group is a molecule that covalently binds to the hydrophobic interacting group. Preferably the molecule is hydrophilic. In other embodiments, the hydrophobic interacting groups interact with the physical chemical protecting group through a noncovalent bond. Preferably the interaction occurs by the formation of an inclusion complex.

In still other embodiments of the third or sixth aspects of the invention, the molecule that disrupts an interaction between the physical chemical protecting group and the hydrophobic interacting groups is a molecule that binds to the physical chemical protecting group better than the hydrophobic interacting groups bind to the physical chemical protecting group. Preferably the molecule that disrupts an interaction between the physical chemical protecting group and the hydrophobic interacting groups is a one-end modified polymer domain. Most preferably the one-end modified polymer domain comprises poly(ethylene glycol), and is modified with a perfluorinated hydrocarbon.

In still other embodiments of the third or sixth aspect of the invention, the molecule that disrupts an interaction between the physical chemical protecting group and the hydrophobic interacting groups is a molecule that degrades the linkage between the physical chemical protecting group and the hydrophobic interacting groups, or is a molecule that degrades the physical chemical interacting groups themselves. Most preferably the molecule that degrades the physical chemical interacting groups is α-amylase or amyloglucosidase.

In still another preferred embodiment of the third or sixth aspect of the invention, the polymer domain comprises poly(ethylene glycol), the hydrophobic interacting groups are perfluorinated hydrocarbons, and the chemical protecting group is β-cyclodextrin.

In preferred embodiments of the fourth or seventh aspect of the invention, the organic solvent is removed is by evaporating or diffusing all or part of it.

In a preferred embodiment of the fourth, fifth, seventh, or eighth aspect of the invention, the organic solvent is N-methylpyrrolidone.

By a "hydrophobic interacting group" is a group attached to the water soluble domain of a polymer, that would otherwise not be soluble under physiological conditions were it not attached to the water soluble domain of a polymer.

By a "physical chemical protecting group" is meant a group or a molecule that interacts with a hydrophobic interacting group in a manner such that the hydrophobic interacting groups are prevented from interacting with each other to an extent such that gelation occurs.

By "gelation" is meant the formation of a material into a gelled state. A material is considered to be in a gelled state when its viscosity is at least 10-fold less than its viscosity when in the presence of a physical chemical interacting group or an organic solvent that prevents the hydrophobic interacting molecules of the material from interacting to an extent such that the material is not in a liquid state.

By a "two-end modified polymer domain" is meant a polymer domain that is modified on each end to contain hydrophobic interacting groups. Preferably the polymer domain comprises PEG.

By a "one-end modified polymer domain" is meant a polymer domain that is modified on only one end to contain a hydrophobic interacting group. Preferably the polymer domain comprises PEG.

By "disrupts" is meant prevents the interaction of two molecules, for example, two hydrophobic interacting groups of a polymer. Preferably the interaction between two hydrophobic interacting groups is sufficient such that the polymer does not form a hydrogel.

As used herein, by "prevents" is meant inhibiting the interaction of hydrophobic interacting groups of a polymer in a hydrogel precursor composition, thereby inhibiting gelation of the composition. Preferably the interaction of the hydrophobic interacting groups is prevented such that the viscosity of the composition is at least 10-fold less than its viscosity when in the presence of a physical chemical protecting group or an organic solvent that inhibits the interaction of the hydrophobic interacting molecules of the material, to an extent such that the composition is not in a liquid state.

By a "stable linkage" is meant a linkage in a material that is cleaved, whether by hydrolysis or oxidation, at a rate slower than the rest of the material is degraded, or otherwise cleared from a site or the body.

By a "stable linkage" is meant a linkage in a material that is cleaved, whether by hydrolysis or oxidation, at a rate that is faster than the rest of the material is degraded or otherwise cleared from a site or the body. The degradation of an unstable linkage determines, at least in part, the overall rate of degradation of the material or its clearance from a site or the body.

By an "inclusion complex" is meant a complex between two components. As used herein, an inclusion complex is formed between a hydrophobic interacting group(s) and a physical protecting group, such that the one component (the hydrophobic interacting group) is partially or wholly surrounded by the second component (the physical chemical protecting group).

By a "sensitive biological material" is meant a material that has biological activity. A sensitive biological material may include, for example, peptides, polypeptides, proteins, synthetic organic molecules, naturally occurring organic molecules, nucleic acid molecules, carbohydrates, lipids, cells, tissues, tissue or cell aggregates, and components thereof.

DETAILED DESCRIPTION

Figure 1:
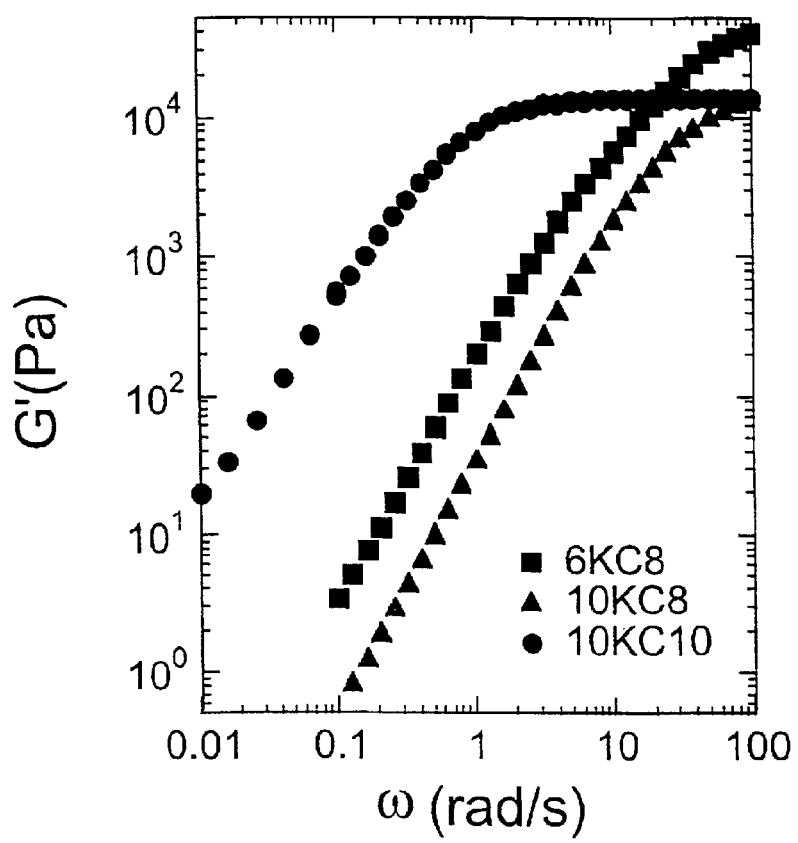
FIG. 1 is a graph illustrating the storage modulus of gel phases in equilibrium at 298° K.
Figure 2:
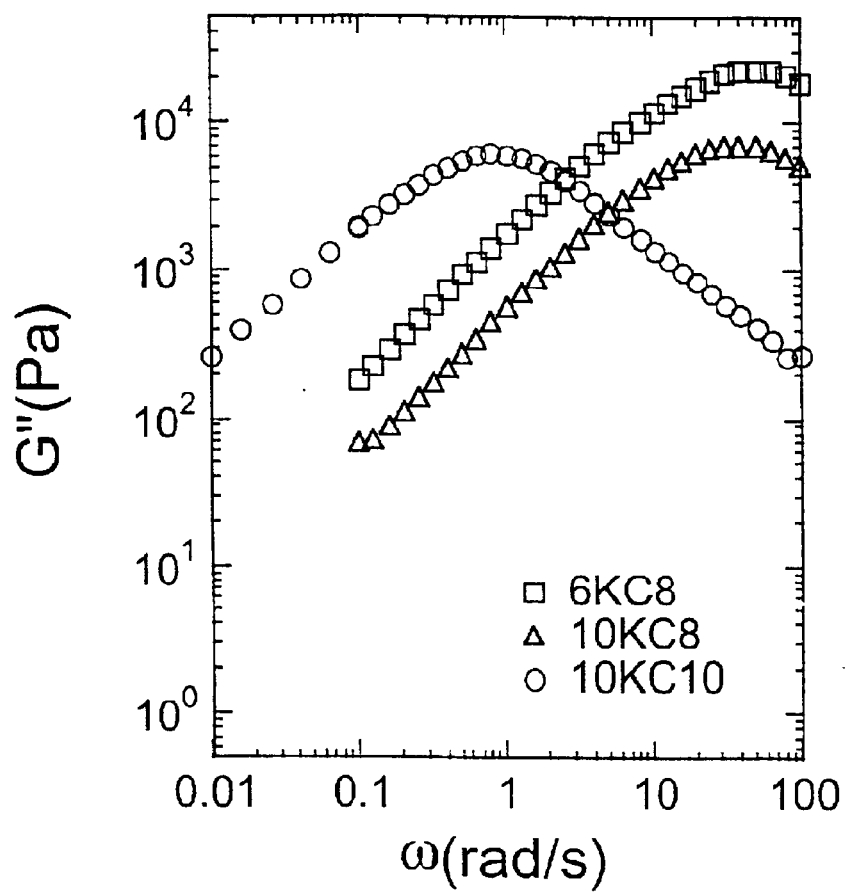
FIG. 2 is graph illustrating the loss modulus of gel phases in equilibrium at 298° K.

The present invention features hydrogels formed by the physical association of polymers in a hydrogel precursor composition. The hydrogel may comprise any hydrophilic (soluble) and biocompatible polymer domain, modified with any hydrophobic interacting groups at two or more sites along the chain (e.g., at the ends or in the domain of the polymer). These hydrophobic interacting groups bind strongly to each other in an interchain manner to form a gel matrix in situ.

An injectable state of the polymer matrix is produced either by the addition of molecules termed "physical chemical protecting groups" that act to disrupt association among the hydrophobic interacting groups of the polymer matrix, or by changing the solvent state to disrupt association among the hydrophobic interacting groups of the polymer matrix.

The injectable state of the hydrogel precursor composition can be switched to a solid hydrogel state by removal of the physical chemical protecting groups after or during delivery to the desired site so that association among the hydrophobic interacting groups is re-established. The physical chemical protecting groups may be removed by their degradation, using, for example, an enzyme, or by addition of a competitor that binds the physical chemical protecting groups, transferring them away from the association sites of the polymer matrix. A PEG molecule with one end modified with a hydrophobic interacting group is one example of a competitor that may be used. The physical chemical protecting groups may also be removed by disrupting the bonds formed between the hydrophobic interacting groups and the physical chemical protecting groups.

The injectable state of the hydrogel precursor composition can also be switched to a solid hydrogel state by changing the solvent conditions to replace a solvent that does not permit association of the hydrophobic interacting groups with a solution that does permit such association. For example, an organic solvent, such as N-methylpyrrolidone (NMP) does not permit association of the hydrophobic interacting groups, but replacing the solvent with an aqueous solution, for example that of a tissue or other body fluid, or evaporating the organic solvent off does permit association.

This novel approach to making polymeric compositions that transition from a liquid state to a solid state is advantageous for the following reasons. It is safe and economical, because it does not involve chemical reactions or the transfer of heat, and it does not require the use of complex instruments and surgical devices that supply both fluids and light to a site. In addition, the hydrogel precursor composition may be applied to a site, for example, a tissue, and formed to the morphology of the site. Another advantage of this method is that a large amount of material may be delivered to a site using minimally invasive surgery, because the material is in a liquid, injectable state.

Polymer Domains

Any polymer domain that is substantially water-soluble may be used in the present invention. Examples of such polymer domains include, but are not limited to, poly (ethylene glycol), poly(vinyl alcohol), poly(vinyl pyrrolidone), poly(ethyl oxazoline), poly(acrylic acid), poly (acrylamide), poly(styrene sulfonate), poly(amino acids), polysaccharides, and copolymers thereof. Each of these polymers presents numerous opportunities for attachment of the hydrophobic interacting groups. For example, initiation and termination of polymerization can be performed so as to obtain good control over the identity of polymer end groups, allowing the hydrophobic interacting groups to be attached thereto.

Alternatively, the hydrophobic interacting groups can be attached as side groups on the polymer domain, either directly by coupling to the side group on the polymer domain (e.g., coupling to the carboxylic acid side groups on poly(acrylic acid)) or indirectly, by coupling to side groups incorporated into the polymer domain by copolymerization (e.g., coupling to carboxylic acid side groups on poly (acrylamide-co-acrylic acid)). For use in the present invention, PEG homopolymers that are approximately 4,000 to 10,000 g/mol are particularly useful.

Hydrophobic interacting groups

Perfluorinated hydrocarbons are the hydrophobic interacting groups that provide for the desired gelation transitions. Preferably the perfluorinated hydrocarbons have the formula $C_nF_{2n+1}CH_2CH_2OH$, where n=6 to 10. Other hydrocarbon groups can also provide these desired gelation interactions, and may be used, although they interact with less affinity than the corresponding perfluorinated hydrocarbon groups.

Connecting Schemes Between the Polymer and the Hydrophobic Interacting Groups

The linkage between the hydrophobic interacting groups and the polymer domain may be selected to be relatively stable or readily degradable. For example, the hydrophobic interacting groups can be attached via anhydride, ester, carbonate, or amide linkages, to make them susceptible to hydrolysis. Oligomeric linkages (e.g. oligomers of lactic, glycolic, or epsilon-caproic acid or oligomers of trimethylene carbonate) can also be incorporated between the polymer chain and the hydrophobic interacting groups. This allows for the regulation of degradation by a process that is hydrolytically controlled. Also, the design and incorporation of such degradable linkages will lead to more predictable toxicology and pathways for elimination of the polymer from the body.

Polymer Conformations

The polymers of the present invention may be linear or branched. A branched conformation may lead to more effective gel formation due to the existence of multiple points for interaction. Thus, multi-arm PEGs (e.g., those PEGs having more than 2 arms) are effective polymer domains. Even more complex branching can be included in the polymer conformations of the invention.

The polymers of the present invention may possess terminal hydrophobic interacting groups or the hydrophobic interacting groups may be incorporated along the polymer domain, either by copolymerization or by copolymerization of a site for secondary grafting of the hydrophobic interacting group. Incorporation of hydrophobic interacting groups along the polymer domain provides for a greater density of hydrophobic interacting groups.

Physical Chemical Protecting Groups

The physical chemical protecting groups may interact with the hydrophobic interacting groups in various ways. For example, the physical chemical protecting groups and the hydrophobic interacting groups may exist as an inclusion complex. Examples of physical chemical protecting groups include, but are not limited to, cyclodextrins, for example, α-, β-, or γ-cyclodextrin. The physical chemical protecting group may be removed by an enzyme, for example, a cyclodextrinase, thus exposing the hydrophobic interacting groups.

Alternatively, a hydrophilic bulky group (the physical chemical protecting group) can be attached beside or on the terminus of the hydrophobic interacting group, with a hydrolytically sensitive linkage. Rapid hydrolysis then triggers a transition from the sol (soluble state) to the gel state. Such a hydrophilic group may be a PEG chain, for example, and the linkage may be a hydrolytically sensitive ester anhydride, amide, carbonate, or oligomeric linkage. This linkage may also be an enzymatically cleavable site, which results in degradation (and thus gelation) after addition of the appropriate enzyme.

Solvents that Prevent Interactions Between Hydrophobic Interacting Groups

Organic solvents may be used to prevent hydrophobic interacting groups from associating, thus prevent gel formation. The injectable state of the hydrogel precursor composition can be switched to a solid hydrogel state by changing the solvent conditions to replace a solvent that does not permit association of the hydrophobic interacting groups with a solution that does permit such association. For example, an organic solvent, such as N-methylpyrrolidone (NMP) does not permit association of the hydrophobic interacting groups. But replacing the organic solvent with an aqueous solution, including that of a tissue or other body fluid, or evaporating the organic solvent off does permit association of the hydrophobic interacting groups. When the solvent exchange is done in vivo, the preferred solvent is NMP (because of the low toxicity). When in vitro solvent exchange is conducted, a number of organic solvents may be used, including, for example, ethyl acetate. Such the solvents may be removed prior to introduction of the hydrogel to an in vivo site.

Alternatively, the organic solvent may be removed by evaporation, thus allowing the precursor hydrogel solution to form a hydrogel. For example, the organic solvent may be evaporated from a solution of polymer and NMP or methylene chloride, resulting in formation of a polymer matrix. Then the polymer matrix may be rehydrated in water, either in vitro or in vivo.

Hydrogels in Contact with Tissues

The hydrogels of the present invention may be formed in contact with a tissue. Preferably the tissue is within a tumor, subcutaneous, intramuscular, adjacent to a tooth, upon the inner or outer surface of an artery or vascular graft, or upon any tissue surface when used to prevent postoperative adhesions.

Incorporation of a Sensitive Biological Material

A sensitive biological material may be incorporated into a hydrogel through the practice of this invention. Examples of sensitive biological materials include, but are not limited to drugs, proteins, peptides, RNA, DNA, inorganic and organic molecules, carbohydrates, lipids, cells, tissues, tissue or cell aggregates, and combinations thereof.

Specific examples of cells that may be incorporated into the hydrogel include, but are not limited to, chondrocytes, endothelial cells, muscle cells, fibroblasts, skin cells, islets of Langerhans, and genetically modified cells for protein delivery.

Specific examples of sensitive biological materials that may be incorporated into the hydrogels include, enzymes, antibiotics, antineoplastic agents, local anesthetics, hormones, antiangiogenic agents, antibodies, neurotransmitters, psychoactive drugs, drugs affecting reproductive organs, oligonucleotides, including antisense oligonucleotides, vasoactive agents, anticoagulants, immunomodulators, cytotoxic agents, antiviral agents, and combinations thereof.

Exemplary sensitive biologicals materials which may be incorporated into the hydrogels of the present invention include growth hormone, for example, human growth hormone, calcitonin, granulocyte macrophage colony stimulating factor (GMCSF), ciliary neurotrophic factor, and parathyroid hormone. Other specific therapeutic agents include parathyroid hormone-related polypeptide, somatostatin, testosterone, progesterone, estradiol, nicotine, fentanyl, norethisterone, clonidine, scopolomine, salicylate, salmeterol, formeterol, albeterol, and valium.

Drugs for the treatment of pneumonia may be used, including pentamidine isothionate. Drugs for the treatment of pulmonary conditions, such as asthma may be used, including albuterol sulfate, β-agonists, metaproterenol sulfate, beclomethasone dipropionate, triamcinolone acetamide, budesonide acetonide, ipratropium bromide, flunisolide, cromolyn sodium, ergotamine tartrate, and protein or polypeptide drugs such as TN antagonists or interleukin antagonists.

Other therapeutic agents include cancer chemotherapeutic agents, such as cytokines, chemokines, lymphokines, and substantially purified nucleic acids, and vaccines, such as attenuated influenza virus. Substantially purified nucleic acids that can be incorporated include genomic nucleic acid sequences, cDNAs encoding proteins, expression vectors, antisense molecules that bind to complementary nucleic acid sequences to inhibit transcription or translation, and ribozymes. For example, genes for the treatment of diseases such as cystic fibrosis, for example, cystic fibrosis transmembrane regulator can be administered. Polysaccharides, such as heparin, can also be administered.

Further therapeutic agents include tissue plasminogen activator (t-PA), superoxide dismutase, catalase luteinizing hormone releasing hormone (LHRH) antagonists, IL-11 platelet factor, IL-4 receptor, enbrel, IL-1 receptor antagonists, TNF receptor fusion proteins, megakaryocyte growth and development factor (MGDF), stemgen, anti-HER-2 and anti-VEGF humanized monoclonal antibody, anti-Tac antibody, GLP-1 amylin, and GLP-1 amylin analogues.

Additional therapeutic agents include atrial natriuretic factor, atrial natriuretic peptide, beta-human chorionic gonadotropin, basic fibroblast growth factor, bovine growth hormone, bone morphogenetic protein, B cell stimulating factor-1, B cell stimulating factor-2, bovine somatotropin, carcinobreaking factor, cartilage induction factor, corticotropin releasing factor, colony stimulating factor, differentiating factor-1, endothelial cell growth factor, erythroid differentiation factor, elongation factor 1-alpha, epidermal growth factor, erythropoietin, thrombopoietin, thymopoietin, fibroblast growth factor, follicle stimulating hormone, granulocyte colony stimulating factor, glial fibrillary acidic protein, growth hormone releasing factor, human alpha-1 antitrypsin, human atrial natriuretic factor, human chorionic gonadotropin, human leukemia inhibitory factor, hemopoietin-1, hepatocyte growth factor, human transforming growth factor, human thyroid-stimulating hormone, interferon, immunoglobulin A, immunoglobulin D, immunoglobulin E, insulin-like growth factor-i, insulin-like growth factor-II, immunoglobulin G, immunoglobulin M, interleukin-1, interleukin-2, interleukin-3, interleukin-4, interleukin-5, interleukin-6, kidney plasminogen activator, lectin cell adhesion molecule, luteinizing hormone, leukemia inhibitor factor, monoclonal antibody, macrophage activating factor, macrophage cytotoxic factor, macrophage colony stimulating factor, megakaryocyte colony stimulating factor, tumor necrosis factor, macrophage inhibitory factor, Mullerian inhibiting substance, megakaryocyte stimulating factor, melanocyte stimulating factor, neutrophil chemotactic factor, nerve growth factor, novel plasminogen activator, nonsteroidal anti-inflammatory drug, osteogenic factor extract, antitumor lymphokine, prostate-specific antigen, anti-platelet activating factor, plasminogen activator inhibitor, platelet-derived growth factor, platelet-derived wound healing formula, plasmatic human interleukin inducing protein, tumor angiogenesis factor, tissue control factor, T cell growth factor, T cell modulatory peptide, transforming growth factor, tumor growth inhibitor, tumor inhibiting factor, tissue inhibitor of metalloproteinases, tumor necrosis factor, tissue plasminogen activator, thyroid stimulating hormone, urokinase-plasminogen activator, vascular endothelial growth factor, and vasoactive intestinal peptide.

Drugs may be dissolved or suspended as precipitates within the polymer form in its dissociated state. This dissociated state can be converted into the associated hydrogel state by any of the methods described above, e.g., by solvent exchange, by drying, by degradation of a protecting group, or by competitive displacement of a protecting group.

As a specific example, the associating polymers are dissolved in dichloromethane at about 40% by weight and a protein drug is added as a suspension. The solution is dried by evaporation to form a film or particles. The dry polymer-protein depot is then re-hydrated by addition of a limited amount of buffered saline (e.g., an amount necessary to bring the material to its equilibrium swelling state). The material is injected, for example, as a particulate, or placed in a tissue site to release its drug.

As a second specific example, the associating polymers are dissolved in NMP at about 50% by weight and the protein is added as a suspension. The polymer-protein-NMP mixture is injected into a tissue site, whereupon diffusion of the NMP from the system and counter-diffusion of water into the system results in a swollen gel depot. Alternatively, the NMP is exchanged against water away from a tissue site, to produce a swollen material that is then injected as a particulate, or placed in a tissue site.

In both of the above examples, the protein is released by diffusion from the depot, with some contribution to the release process also being given by dissolution of the material from the surface of the depot.

EXAMPLE 1

Synthesis of End-Group Modified PEGs

Poly (ethylene glycol) (PEG) of nominal molecular weight 6000 g/mol (6K) (from Fluka), 10K (from Aldrich), and 20K (from Fluka) were used. Three different fluorinated alcohols ($C_nF_{2+1}CH_2CH_2OH$, where n=6, 8, 10) were purchased from Lancaster Synthesis Inc. Isophorone diisocyanate (IPDI), dibutyltin diacetate and anhydrous tetrahydrofuran (THF) were purchased from Aldrich.

The method of Glass et al. (Kaczmarski and Glass, Macromolecules, 26:5149–5156, 1993) was used to attach the perfluorinated end groups to the terminal hydroxyls of PEG. PEG was dried by azeotropic distillation in toluene, and was reacted with 100 fold molar excess (with respect to end-groups) of vacuum-distilled IPDI in anhydrous THF for 48 hours. This intermediate was precipitated in anhydrous ethyl ether to remove unreacted IPDI, and was subsequently reacted with a 10-fold excess of perfluoroalcohol in anhydrous THF for 48 hours. Dibutyltin diacetate was added for the second step. The reaction mixture was precipitated in anhydrous ethyl ether, then dissolved in THF, and reprecipitated to form the final two-end modified PEG molecules that contain hydrophobic interacting groups. All reactions were done under argon purge.

One-end modified PEG molecules can be generated using a monomethoxy PEG, and keeping the molar ratios in the reaction the same as those described above.

The degree of substitution was determined by $^{19}F$ NMR using $CF_3COOH$ or $CF_3SO_3Na$ as an internal standard with a 5 second delay time (i.e., long enough to get the integral value independent of the delay time between pulses). The samples prepared for this study are described in Table 1, where nKCm is the sample, in which nK denotes the PEG molecular weight and Cm denotes the length of the $C_mF_{2m+1}CH_2CH_2OH$ group.

For a given PEG, each sample modified with $C_{10}F_{21}$ was checked by reverse phase HPLC. A C18 column was used with the Water HPLC system with a gradient input of mixed solvent (ranging from 20:80 of acetonitrile:ethanol to 100% acetonitrile) that can separate unmodified, one-end modified, and two-end modified samples. Good agreement between the values obtained by HPLC (in parenthesis in the final column of Table 1) and the values obtained by $^{19}F$ NMR support the reliability of the NMR method.

TABLE 1

Reaction extent of two-end modified PEGs

| Sample | PEG-block | End-group | Degree of substitution (%) |
|---|---|---|---|
| 6KC10 | 6 kg/mol | —$(CH_2)_2$—$C_{10}F_{21}$ | 97 (97) |
| 6kC8 | 6 kg/mol | —$(CH_2)_2$—$C_8F_{17}$ | 89 |
| 6KC6 | 6 kg/mol | —$(CH_2)_2$—$C_6F_{13}$ | 99 |
| 10KC10 | 10 kg/mol | —$(CH_2)_2$—$C_{10}F_{21}$ | 94 (96) |
| 10KC8 | 10 kg/mol | —$(CH_2)_2$—$C_8F_{17}$ | 94 |
| 20KC10 | 20 kg/mol | —$(CH_2)_2$—$C_{10}F_{21}$ | 97 (92) |
| 20KC8 | 20 kg/mol | —$(CH_2)_2$—$C_8F_{17}$ | 96 |

EXAMPLE 2

Formation of Hydrogel Phases

The phase behavior of two-end modified PEGs was governed by the relative length of the PEG chain and the perfluorinated hydrocarbon end groups (Table 2). Some of the two-end modified PEGs showed phase separation and others did not. This phase separation phenomenon can provide useful applications for these transition systems; when this system is used as a delivery device in the open system, it will maintain the high modulus matrix of the equilibrium composition, compared to the systems using materials which do not show the phase separation, since the matrix formed from these would be dissolved with continuous lowering of the modulus for the same concentration of polymers.

Among the two-end modified PEGs synthesized, 6KC10 did not exist as a homogeneous phase in water, rather only as a slightly swollen precipitate. At the other extreme, 20KC10 and 20KC8 existed as homogeneous solutions over the whole range of polymer concentrations, though the viscosity increased drastically as the concentration of polymer increased. Polymers that were in between 6KC 10 and 20KC8 in terms of the relative length of PEG to the hydrophobic end groups, for example, 6KC6, 6KC8, 10KC8, and 10KC10, showed phase separation into a gel coexisting with a sol (soluble liquid phase) in water and in phosphate buffered saline (PBS) solution. Increasing the temperature did not lead to any noticeable change of the gel phase concentration for the phase separating systems; the phase boundary was almost temperature-invariant. But, some increase of the gel phase concentration was observed for 10KC8 above 60° C.

The gel properties, such as modulus and transport properties (diffusion coefficient and viscosity) were sensitive to the degree of swelling of the gel (the inverse of the gel phase concentration). Increasing the length of the PEG chain increased the swelling ratio of the gel, since it is analogous to reducing the crosslink density. When the PEG length was fixed and the length of the hydrophobic interacting group was varied, the swelling ratio was nearly constant (compare 10KC10 to 10KC8; and compare 6KC8 to 6KC6). The swelling ratio increased, however, with PEG length (compare 6KC8 to 10KC8).

The low concentration of the dilute phase (sol phase) means that a small driving force for the degradation of these gels would be present when they are exposed to an open system (e.g., as an implant) in the case of diffusion in the dilute phase to be rate-determining step, compared to the systems which do not show phase separation for the same concentration of polymers.

The behavior of the polymers in deionized water versus phosphate buffered saline (PBS) showed that the gel concentration was slightly higher in PBS than in water, and the sol concentration was consistently lower in PBS than in water. This difference was due to the decrease of solvation of PEG chains from a salting out effect and the increase of aggregation tendency of fluorocarbon end groups by the added salts in the PBS solution (Zhang et al, Abstract of the American Chemical Society Meeting, 213, 236, 1997; and Bailey et al., J. Appl. Polym. Sci. 1:56–62, 1959). The effect of dissolved electrolytes will be present in vivo, with the beneficial effects of increasing the modulus and reducing the rate of dissolution.

TABLE 2

Phase behaviors and compositions of phases of modified PEGs

| sample in PBS (wt %) | type of phase behavior | equilibrium compositions in water (wt %) | | equilibrium compositions in PBS (wt %) | |
|---|---|---|---|---|---|
| | | gel conc., $C_{gel, eq}$ | sol conc., $C_{sol, eq}$ | gel conc., $C_{gel, eq}$ | sol conc., $C_{sol, eq}$ |
| 20KC8 | 1 phase | N/A | N/A | N/A | N/A |
| 20K10 | 1 phase | N/A | N/A | N/A | N/A |
| 10KC8 | 2 phase | 6.5 ± 0.2 | 0.075 ± 0.005 | 7.8 ± 0.2 | 0.055 ± 0.002 |
| 10KC10 | 2 phase | 6.8 ± 0.7 | 0.019 ± 0.008 | 8.1 ± 0.7 | 0.011 ± 0.003 |
| 6KC6 | 2 phase | 9.5 ± 0.5 | 0.066 ± 0.007 | 10.5 ± 0.6 | 0.038 ± 0.002 |
| 6KC8 | 2 phase | 11.0 ± 0.3 | 0.042 ± 0.007 | 12.5 ± 0.3 | 0.017 ± 0.001 |
| 6KC10 | insoluble | N/A | N/A | N/A | N/A |

EXAMPLE 3

Rheological Properties of Gel Phases

Rheological measurements were made to gain initial insight into gel structure (Table 3). Previous work by Annable, et al., (J. Rheology 37:695–726, 1993) showed that the PEG systems modified with hydrocarbon tails were governed by a single relaxation time. Thus, these systems can be well described by a simple Maxwell model.

The gel phases of all the systems showing phase separations were still governed by the single relaxation behavior. A similar order of magnitude of infinite modulus ($G_\infty$, $10^4$ Pa) was observed for 10KC10 and 10KC8, indicating the similar density of physical junctions within these two gels, which coincide with similar values of swelling ratios. A higher value was observed for 6KC8, meaning a higher density of physical junctions was present, which also agrees with the smaller swelling ratio. The large difference in relaxation time between 10KC10 and 10KC8 showed that the addition of one $CF_2$ unit significantly increases the strength of physical junctions, resulting in a longer relaxation time.

TABLE 3

Relaxation times of gel phases in equilibrium at 298K

| | 10KC10 | 10KC8 | 6KC8 |
|---|---|---|---|
| Relaxation time (sec) | 1.14 | 0.028 | 0.021 |

EXAMPLE 4

Disruption of a Gel by β-CD (Induction to the Injectable State)

Cyclodextrins (CDs) are cyclic starches consisting of 6, 7, or 8 a-1,4linked glucose monomers called α, β, and γ-cyclodextrin, respectively. These molecules are ring or torus-shaped and possess a hydrophobic cavity and a hydrophilic exterior. The partial hydrophobic nature of CD allows it to associate with nonpolar organic moieties or molecules to form inclusion complexes (Shieh et al., Pure Appl. Chem. A33:673–683, 1996).

Complex formation between α, β, and γ-CD and perfluorocarbon surfactants showed that β-CD has the largest association constants among the cyclodextrins for a given hydrophilic head. For long fluorocarbon surfactants ($C_mF_{2-1}Na$, where $m \geq 7$), it is even possible for two β-CD molecules to bind to each surfactant molecule (Guo et al., Langmuir 8:446–451, 1992). Based on the association between β-CD and the fluorocarbon surfactants, the addition of β-CD to solutions of one end-modified PEG (modified with perfluorinated groups) reduced the viscosity of the solution (Zhang, et al., Abstract of the American Chemical Society Meeting, 211:166-Poly, 1996).

If the complexation of β-CD to the fluoro end groups of two-end modified PEG is sufficient to hide the hydrophobicity of the end groups, the gel phase will not be formed. Mixing a saturated aqueous solution of β-CD and the gel phase of 10KC10 caused the disappearance of the gel-phase. In addition, adding a one-fold molar ratio excess of β-CD to end groups to 10KC10, applying water, and shaking the solution resulted in low viscosity solutions. These results indicated that β-CD can effectively prevent the hydrophobic interacting groups of the polymer from strongly associating with each. The solution was not clear, especially for the higher concentration of solutes, and the apparent viscosity was much higher than the same concentration of unmodified pure PEG solution, so it appears that there may be weak or local associations among the β-CD-complexed polymers. Nevertheless, the addition of cyclodextrin to the polymers is enough to transition the gel to an injectable state.

EXAMPLE 5

Reformation of a Gel by Enzymatic Degradation of β-CD

There are several sources of enzymes that can degrade cyclodextrin. Most of them are from microbial sources, but enzymes from saliva and the pancreas can also effectively degrade γ-CD and to a lesser extent β-CD (Saha et al., Starch/Starke 44:312–315, 1992), α-amylase from *aspergillus oryzae* can degrade β-CD (Jordal et al, Starch/Starke 36:104–143, 1984), although it is a relatively poor cyclodextrinase.

Two enzymes were tested for their ability to degrade cyclodextrin in the system described herein: α-amylase from *aspergillus oryzae* (crude powder), and amyloglucosidase from *aspergillus niger* (solution in 1 M glucose), both purchased from Sigma. In one study, 0.008 g of α-amylase (from *aspergillus oryzae*) was added to 0.55 g of the homogeneous complex solution of 10KC8 and β-CD (7.73 weight % for 10KC8, and 3.35 weight % for p-CD). After shaking to mix, the sample was kept at 37° C. The sample started to become viscous upon mixing, and after 20 minutes, it exhibited a gel-like structure.

In a second study, 0.065 g of the enzyme solution amyloglucosidase (from *aspergillus niger*) was added to 0.513 g of the precursor solution (7.59 weight % for 10KC8, and 3.27 weight % for β-CD). After 30 minutes, the sample started to become viscous, and after 70 minutes, it became insoluble.

EXAMPLE 6

Reformation of a gel by Transfer of CD to a One-End Modified PEG

PEGs modified to contain a hydrophobic interacting group on only one end will form a micelle-like structure in aqueous solutions, and in this structure they are injectable even when present below the critical transition concentration. Furthermore, the affinity of a one-end modified PEG having a small molecular weight of a PEG for CD is greater than the affinity of a two-end modified PEG having a large molecular weight of PEG for CD (Amiel et al., J. Inclusion Phen. & Mol. Recog., 25:61–67, 1996). Thus, mixing a CD-complexed, two-end modified PEG solution and an appropriate amount of a one-end modified PEG solution will result in the transfer of the majority of β-CD from the two-end modified PEG to the one-end modified PEG by mass action and the higher tendency to make inclusion complexes with the one-end PEG. The removal of β-CD from the two-end modified PEG then reveals the hydrophobic interacting groups of the two-end modified PEGs, and, if the concentration of the added one-end modified PEG is not so high as to break down the physical junction by the surfactant action of the excess bare one-end modified PEG, the mixture will form a gel structure again.

With 10KC10 as a gel-forming agent, 5K-M-C10 and 2K-M-C10 (where M denotes that only one end is modified with a perfluorinated group) were explored as CD-transfer inducing agents. First, a 5 weight % solution of 10KC10, coupled with CDs, and a 10.2 weight % solution of 5K-M-C10 solution were mixed together in equal amounts. The mixture exhibited a marked enhancement of viscosity, but did not form a gel state (where the gel state was determined by whether there was a noticeable flow of solution when the vial containing it was inverted).

Next, using 2K-M-C 10 and 10KC10, the mixing ratios were varied from 1:1 to 1:3 (10KC10:2K-M-C10, in molar concentration), keeping the total concentrations of the reactants constant at 6.3 weight %. Among these mixtures, the 1:2 ratio gave the most gel-like state, which was maintained up to a temperature of 37° C. A 1:2 molar ratio mixture of 10KC 10-CD complex solution (0.073 g/ml, polymer/water) and 18.2 weight % of 2K-M-C10 solution resulted in reversion to a gel structure. For 10KC8, a 1:1 molar ratio was sufficient to induce the gel phase since CD transfers more easily from the C8 end group of the two-end modified PEG to the C10 end group of the one-end modified PEG.

EXAMPLE 7

Dissolution Characteristics of Gel Phases

Dissolution rates of gel phases are measured by direct measurements of dissolved amounts of polymers, or by the shift of the surface plasmon resonance angle of ultrathin gold film coated with the thin film of the polymer matrix that is exposed to the flow of water (Aust et al., TIP 2:313–32, 1994). For the transition system showing phase separations, the compositions of the polymer matrix are the equilibrium gel concentrations. To compare the phase separation system with the system with no phase separation, the dissolution rates of 10 weight % of 20KC10 and 12.8 weight % of one-end modified 5K-M-C10, which shows a lyotropic gel phase transition at that concentration, were measured (Table 4).

TABLE 4

Dissolution rates of polymer matrix

|  | 10KC10 | 10KC8 | 6KC8 | 20KC10 | 5K-M-C10 |
|---|---|---|---|---|---|
| Conc. (wt %) | (6.8 wt %) | (6.5 wt %) | (11.0 wt %) | (10.0 wt %) | (12.8 wt %) |
| Dissolution rate (mg/cm$^2$/hr) | not measurable | $1.67 \times 10^{-3}$ | $3.33 \times 10^{-4}$ | 0.168 | 0.201 |

As expected, the systems which did not show phase separation (20KC 10 and 5K-M-C 10) exhibited much faster dissolution rates than those with phase-separation (100 times faster rates of 20KC10 than that of 10KC8). Of the phase-separating systems examined, 6KC8 showed around 5 times slower dissolution rates than 10KC8, and the rate of 10KC10 dissolution was much slower than 6KC8. The absolute small value of dissolution rates for the phase separating species confirmed that these species can be used as delivery carriers in the open system. Also, by choosing the right ratio of hydrophilic and hydrophobic groups, the degradation rate of the matrix can be controlled.

Another feature of polymer matrix degradation is whether the matrix is degraded homogeneously or heterogeneously. Maintaining the constant resonance angle for the phase separating species until the film is thin enough so that the thickness affects the resonance angle denotes that no change in the refractive index of the polymer matrix. This means that the hydrogels degrade heterogeneously (i.e., from the surface inward). Such a heterogeneous degradation characteristic is beneficial for the application of delivery of a sensitive biological material, because the drug can exhibit a liner (i.e., zero order) release profile. Thus using the systems of this invention, the constant release of a drug is achievable.

EXAMPLE 8

Disruption of a Gel by Addition of Organic Solvents

Associative interactions of polymers through their hydrophobic interacting groups may be disrupted by altering the characteristics of the solvent that the polymers are contained in, and these interactions may be re-established by altering the solvent again. Disrupting the associative interactions of the polymer can be achieved, for example, by dissolving the gel-forming polymer in a water mixture with a water-soluble organic solvent, such as NMP, or in the organic solvent neat, and then converting the non-associative state into the associated state by removal of the solvent and addition of water. This may be accomplished in a number of ways. A flowable solution of the polymer in NMP or an NMP-water mixture (in the non-associated state) may be contacted with an aqueous environment, permitting the diffusion of the NMP from the polymer solution and its corresponding replacement by water, thus converting the material into an associative state.

Alternatively, the material in the NMP or NMP-water mixture may be injected into a tissue site, and the NMP allowed to exchange with the aqueous component of the body fluids, to achieve the same end. When the exchange is conducted in vivo, the preferred solvent is NMP, the toxicity of which is very low, although other solvents, including ethyl acetate, may also be useful. When the exchange is conducted in vitro, for example, for the encapsulation of drugs, a wide variety of solvents are available, since the solvent may be removed before introduction into the body. Alternatively, the solvent may be removed by evaporation, such as by drying a solution of the polymer from NMP or methylene chloride, followed by rehydration in water, either in vitro or in vivo.

Figure 3:
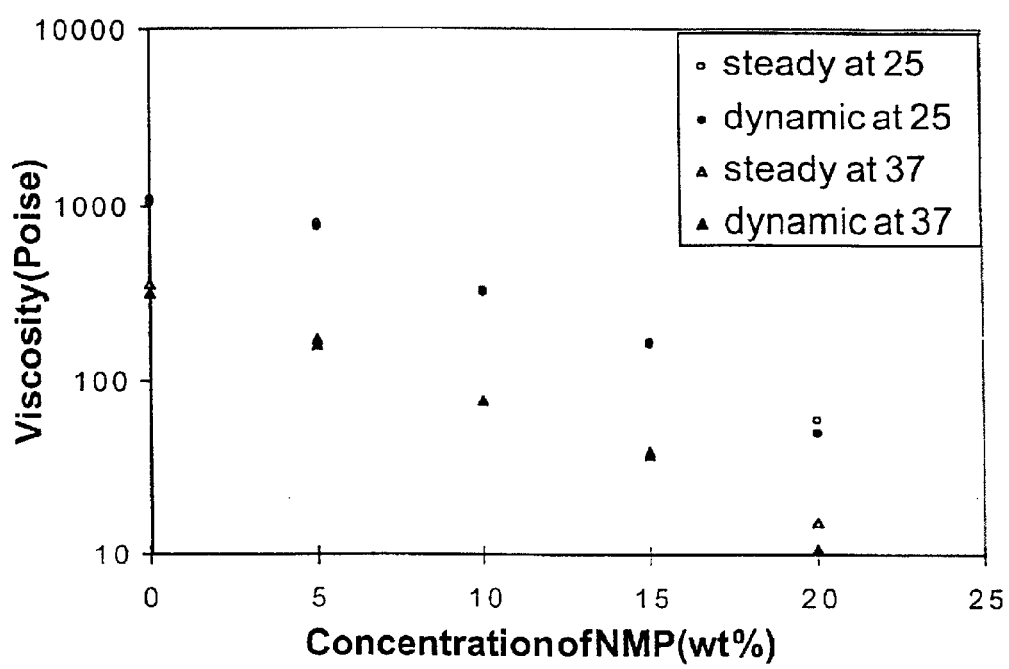
FIG. 3 is a graph illustrating the viscosity change of 10KC8 in aqueous solution, induced by addition of N-methylpyrrolidone (NMP) to disrupt the association of 10KC8.

As evidence that the associated state may be disrupted by the addition of an organic solvent, the viscosity of a 8% solution of 10KC8 in water was measured. Varying concentrations of NMP were added to this solution, and a dramatic reduction in the viscosity of the system was observed, as illustrated in FIG. 3.

Figure 4:
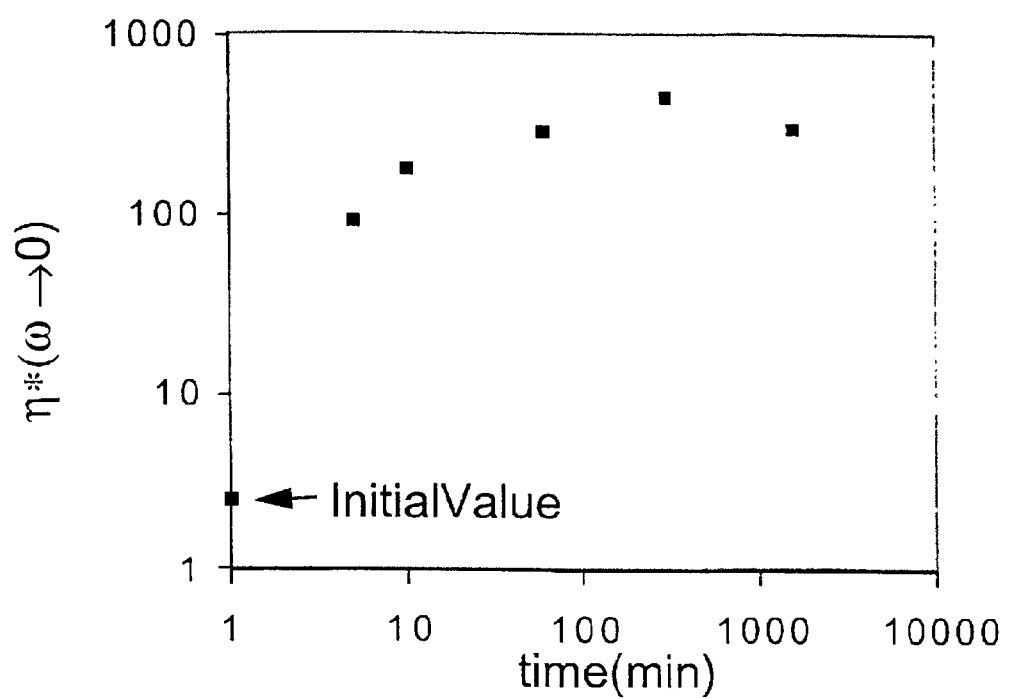
FIG. 4 is a graph illustrating the re-establishment of the associated state of 10KC8 by solvent exchange, from NMP to water.

As evidence that the associated state may be restored by the exchange of an organic solvent, a 50% solution of 10KC8 in NMP was placed within a reservoir of water, the thickness of the initial sample was approximately 1.5 mm. For this system, the steady viscosity of the sample increased dramatically by more than two orders of magnitude, as shown in FIG. 4.

All publications mentioned in this specification are herein incorporated by reference to the same extent as if each independent publication or patent application was specifically and individually indicated to be incorporated by reference.

What is claimed is:

1. A hydrogel precursor composition comprising:
    (a) a polymer comprising a water soluble polymer domain with at least two hydrophobic interacting groups attached thereto, wherein said hydrophobic interacting groups bind strongly to each other in an interchain manner to form a hydrogel under physiological conditions; and
    (b) a physical chemical protecting group that inhibits gel formation of said polymer by preventing said hydrophobic interacting groups from binding strongly in an interchain manner, wherein said physical chemical protecting group is a cyclodextrin.

2. A hydrogel or hydrogel precursor composition comprising:
    (a) a polymer comprising a water soluble polymer domain with at least two hydrophobic interacting groups attached thereto, wherein said hydrophobic interacting groups bind strongly to each other in au interchain manner to form a hydrogen under physiological conditions;
    (b) a physical chemical protecting group that inhibits gel formation of said polymer by preventing said hydrophobic interacting groups from binding strongly in an interchain manner, wherein said physical chemical protecting group is a cyclodextrin; and
    (c) a molecule that disrupts an interaction between said physical chemical protecting group and said hydrophobic interacting groups.

3. The hydrogel precursor composition of claim 1, wherein said polymer domain comprises poly(ethylene glycol), poly(vinyl alcohol), poly(vinyl pyrrolidone), poly(ethyl oxazoline), poly(acrylic acid), poly(acrylamide), poly(styrene sulfonate), poly(amino acids), polysaccharides, or copolymers thereof.

4. The hydrogel precursor composition of claim 1, wherein said physical chemical protecting group is β-cyclodextrin.

5. The hydrogel precursor composition of claim 1, wherein said hydrophobic interacting groups are positioned at the termini of said polymer domain.

6. The hydrogel precursor composition of claim 1, wherein said hydrophobic interacting groups are positioned within said polymer domain.

7. The hydrogel precursor composition of claim 1, wherein said hydrophobic interacting groups are hydrocarbons.

8. The hydrogel precursor composition of claim 5, wherein said hydrocarbons are perfluorinated hydrocarbons.

9. The hydrogel precursor composition of claim 1, wherein said polymer domain comprises poly(ethylene glycol) and said hydrophobic interacting groups are perfluorinated hydrocarbons.

10. The hydrogel or hydrogel precursor composition of claim 2, wherein said molecule that disrupts an interaction between said physical chemical protecting group and said hydrophobic interacting groups is a molecule that binds to said physical chemical protecting group better than said hydrophobic interacting groups binds to said physical chemical protecting group.

11. A method for forming a hydrogel in contact with a tissue, said method comprising the steps of:
    (a) providing a solution comprising a polymer comprising a water soluble polymer domain having at least two hydrophobic interacting groups attached thereto, wherein said hydrophobic interacting groups bind strongly to each other in an interchain manner to form a hydrogel under physiological conditions, and a physical chemical protecting group that inhibits gel formation of said polymer by preventing said hydrophobic interacting groups from binding strongly in an interchain manner, wherein said physical chemical protecting group is cyclodextrin;
    (b) providing a molecule that disrupts an interaction between said physical chemical protecting group and said hydrophobic interacting groups;
    (c) combining said solution of step (a) with said molecule of step (b) to form a mixture, wherein prior to, during, or after said combining, said solution and said molecule are contacted with a tissue; and
    (d) allowing gel formation of the solution of the mixture of step (c) in contact with said tissue.

12. A method for forming a hydrogel in contact with a tissue, said method comprising the steps of:
    (a) providing a solution comprising a polymer comprising a water soluble polymer domain having at least two hydrophobic interacting groups attached thereto, wherein said hydrophobic interacting groups bind strongly to each other in an interchain manner to form a hydrogel under physiological conditions, and a water soluble organic solvent, said organic solvent preventing gel formation of said polymer; and
    (b) removing all or part of said organic solvent from said solution, wherein prior to, during, or after said removal, said solution is contacted with a tissue,
    wherein said removing of said organic solvent in step (b) allows said hydrophobic interacting groups to bind strongly to each other in said interchain manner to form said hydrogel in contact with said tissue.

13. A method for forming a hydrogel in contact with a tissue, said method comprising the steps of:
    (a) providing a solution comprising a polymer comprising a water soluble polymer domain having at least two hydrophobic interacting groups attached thereto, wherein said hydrophobic interacting groups bind strongly to each other in an interchain manner to form a hydrogel under physiological conditions, and a water soluble organic solvent, said organic solvent preventing gel formation of said polymer; and
    (b) contacting said solution with a tissue; and
    (c) allowing at least a portion of said organic solvent to be removed from said solution, wherein said removal of said organic solvent allows said hydrophobic interacting groups to bind strongly to each other in said interchain manner to form said hydrogel in contact with said tissue.

14. A method for incorporating a sensitive biological material into a hydrogel composition, said method comprising the steps of:
    (a) providing a solution comprising a polymer comprising a water soluble polymer domain having at least two hydrophobic interacting groups attached thereto, wherein said hydrophobic interacting groups bind strongly to each other in an interchain manner to form a hydrogel wider physiological conditions, and a physical chemical protecting group that inhibits gel formation of said polymer by preventing said hydrophobic interacting groups from binding strongly in an interchain manner, wherein said physical chemical protecting group is a cyclodextrin;

(b) providing a molecule that disrupts an interaction between said physical chemical protecting group and said hydrophobic interacting groups;

(c) providing a sensitive biological material;

(d) combining said solution with said molecule and said sensitive biological material to form a mixture; and (e) allowing gel formation of the mixture of step (d).

15. A method for incorporating a sensitive biological material into a hydrogel composition, said method comprising the steps of:

(a) providing a solution comprising a polymer comprising a water soluble polymer domain having at least two hydrophobic interacting groups attached thereto, wherein said hydrophobic interacting groups bind strongly to each other in an interchain manner to form a hydrogel under physiological conditions, and a water soluble organic solvent, said organic solvent preventing gel formation of said polymer;

(b) providing a sensitive biological material; and (c) combining said sensitive biological material with said solution to form a mixture, wherein prior to, during, or after, said combining, all or part of said organic solvent is removed from said solution;

wherein said removal of said organic solvent allows said hydrophobic interacting groups to bind strongly to each other in said interchain manner to form said hydrogel.

16. The method of claim 13, wherein said organic solvent is removed by evaporation.

17. The method of claim 13, wherein said organic solvent is removed by diffusion into a bodily fluid.

18. The method of claim 13, wherein said organic solvent is removed by diffusion into an aqueous solution.

* * * * *